US00PP12733P2

(12) United States Plant Patent
van der Voort

(10) Patent No.: US PP12,733 P2
(45) Date of Patent: Jun. 25, 2002

(54) LILY PLANT NAMED 'MEDUSA'

(75) Inventor: Cees A. van der Voort, Katwijk (NL)

(73) Assignee: Vletter & Den Haan Beheer B.V., Rijnsburg (NL)

( * ) Notice: Subject to any disclaimer, the term of this patent is extended or adjusted under 35 U.S.C. 154(b) by 0 days.

(21) Appl. No.: 09/357,102

(22) Filed: Jul. 19, 1999

(51) Int. Cl.[7] ..... A01H 5/00
(52) U.S. Cl. ..... Plt./315
(58) Field of Search ..... Plt./315

(56) References Cited

PUBLICATIONS http://www.user.netland.nl/~hanns//exit4.html, p. 4, May 1996.*
UPOV–ROM GTITM Computer Database 2000/02, GTI Jouve Retrieval Software, citation for 'Medusa', 1993.*
Plant Breeder's Rights application in The Netherlands (Dec. 16, 1993).
Plant Breeder's Rights denomination in The Netherlands (Nov. 5, 1993).
Plant Breeder's Rights certificate in The Netherlands (May 16, 1995).

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Lily plant named 'Medusa' characterized by having upright flowers, reddish pink color, and contrasting yellow-green mid-vein in the flower bowl.

1 Drawing Sheet

BACKGROUND OF THE INVENTION

The present invention comprises a new and distinct cultivar of lily plant, botanically known as *Lilium L.*, and hereinafter referred to by the cultivar name 'Medusa'.

'Medusa' is a product of a planned breeding program which had the objective of creating new lily cultivars having large, upright, pink flowers.

'Medusa' was originated from a hybridization made by the inventor, in a controlled breeding program in Rijnsburg, the Netherlands in 1984. The male and female parents were unnamed seedlings of *Lilium L.* oriental hybrids. Both parents are proprietary cultivars used in the breeding program.

'Medusa' was discovered and selected as one flowering plant within the progeny of the stated cross by the inventor, Cees A. van der Voort, on Jun. 7, 1984 in a controlled environment in Rijnsburg, the Netherlands.

The first act of asexual reproduction of 'Medusa' was accomplished when scales were taken from the initial selection in October 1987 in a controlled environment in Rijnsburg, the Netherlands by, or under the supervision of, Cees A. van der Voort. Horticultural examination of selected units initiated in May, 1984 has demonstrated that the combination of characteristics as herein disclosed for 'Medusa' are firmly fixed and are retained through successive generations of asexual reproduction.

BRIEF DESCRIPTION OF THE INVENTION

The following traits have been repeatedly observed and are determined to be basic characteristics of 'Medusa' which in combination distinguish this lily as a new and distinct cultivar:

1. Erect flowers;
2. Reddish pink color; and
3. Contrasting yellow-green mid-vein in the flower bowl.

'Medusa' has not been observed under all possible environmental conditions. The phenotype of the new cultivar may vary significantly with variations in environment such as temperature, light intensity, and daylength without any change in genotype. The following observations, measurements, and comparisons describe plants grown in the Dutch experimental research institute CPRO-DLO, Wageningen, the Netherlands under conditions which approximate those generally used in commercial practice.

Of the many commercial cultivars known to the present inventor, no other cultivars are similar in comparison to 'Medusa'.

BRIEF DESCRIPTION OF THE DRAWING

The accompanying color photographic drawing shows typical plant, and flower characteristics of 'Medusa', with colors being as true as possible with illustrations of this type.

DETAILED BOTANICAL DESCRIPTION

In the following description, color references are made to The Royal Horticultural Society Colour Chart (R.H.S.). The color values were determined between 12 am and 2 pm, in July 1994, at the Dutch experimental research station CPRO-DLO, Wageningen, the Netherlands.

Origin: Seedling from breeding program.
Parentage:
*Female parent.*—Unnamed seedling.
*Male parent.*—Unnamed seedling.

Classification:

*Botanical.*—A hybrid of the genus *Lilium L.*

*Commercial.*—Oriental Lily cv. 'Medusa'.

Plant:

*Form.*—A single stem carrying numerous, alternately arranged pedicels.

*Height.*—High for the mature plant, approximately 110 cm, depending on cultivation conditions.

*Growth habit.*—Vigorous; i.e., approximately 20–30% more vigorous than the traditional 'Stargazer' cultivar.

*Stem.*—Circular in transverse section; anthocyanin pigmentation RHS 200D present in spots and stripes; internodal length 3.8 cm, depending on the cultivation conditions of the cultivar.

*Foliage.*—Quantity: Approximately 65, depending on cultivation conditions. Size of leaf: Mature leaves are approximately 7 cm long and 2 cm wide, depending on cultivation conditions. Shape of leaf: Generally ovate, hardly any pubescence. Color: Medium green RHS 136B.

*Bulb.*—Size: 16 to 18 cm in circumference. Color: White RHS 157B with pink shades.

Bud:

*Form.*—Tapering like a lancet.

*Size.*—Short to medium, 9 cm in length, depending on cultivation conditions.

*Opening.*—Unfolds normally.

*Color.*—Red purple, RHS 67A.

*Tepals.*—Folded, three visible.

Flower:

*Blooming habit.*—Raceme.

*Size.*—Short to medium, 16 cm in diameter, depending on cultivation conditions.

*Borne.*—Upright along a longitudinal axis.

*Shape.*—Generally, hexagonal star in form and bowl-shaped in cross-section.

*Tepalage.*—Number of Tepals: 6. Arrangement: Three inner and three outer. Color: Upper Surface: Pink, RHS 68A; color of mid-vein is green with outer sides of the tepals pink, RHS 68A. Lower Surface: RHS 68B. Spotting or Marking: Spots and markings are present, dark pink in color RHS 61A.

*Pedicel.*—Length: Short to medium, 8 cm, depending on cultivation conditions. Color: RHS 141C. Form: rounded.

*Texture.*—Papillose.

*Disease resistance.*—Average in comparison to the disease resistance level of traditional Lily cultivars.

*Fragrance.*—Present.

*Lasting quality.*—Excellent, the average lasting period is at least 21 days, when cut and kept in a controlled climate in conformity with Dutch Auctions and Research Station standards.

Reproductive organs:

*Stamens and anthers.*—Arrangements: Anthers form a generally circular pattern at their upper ends. Number 6. Length: Short to medium, depending on cultivation conditions. Filaments Color: Green RHS 145B.

*Pollen color.*—Greyed-red, RHS 179A.

*Anther color.*—Reddish brown RHS 179A.

*Pistils.*—Green RHS 144A.

*Stigma.*—Purple RHS 60C.

*Ovaries.*—Triangular in shape.

I claim:

1. A new and distinct cultivar of Lily plant named 'Medusa', as illustrated and described herein.

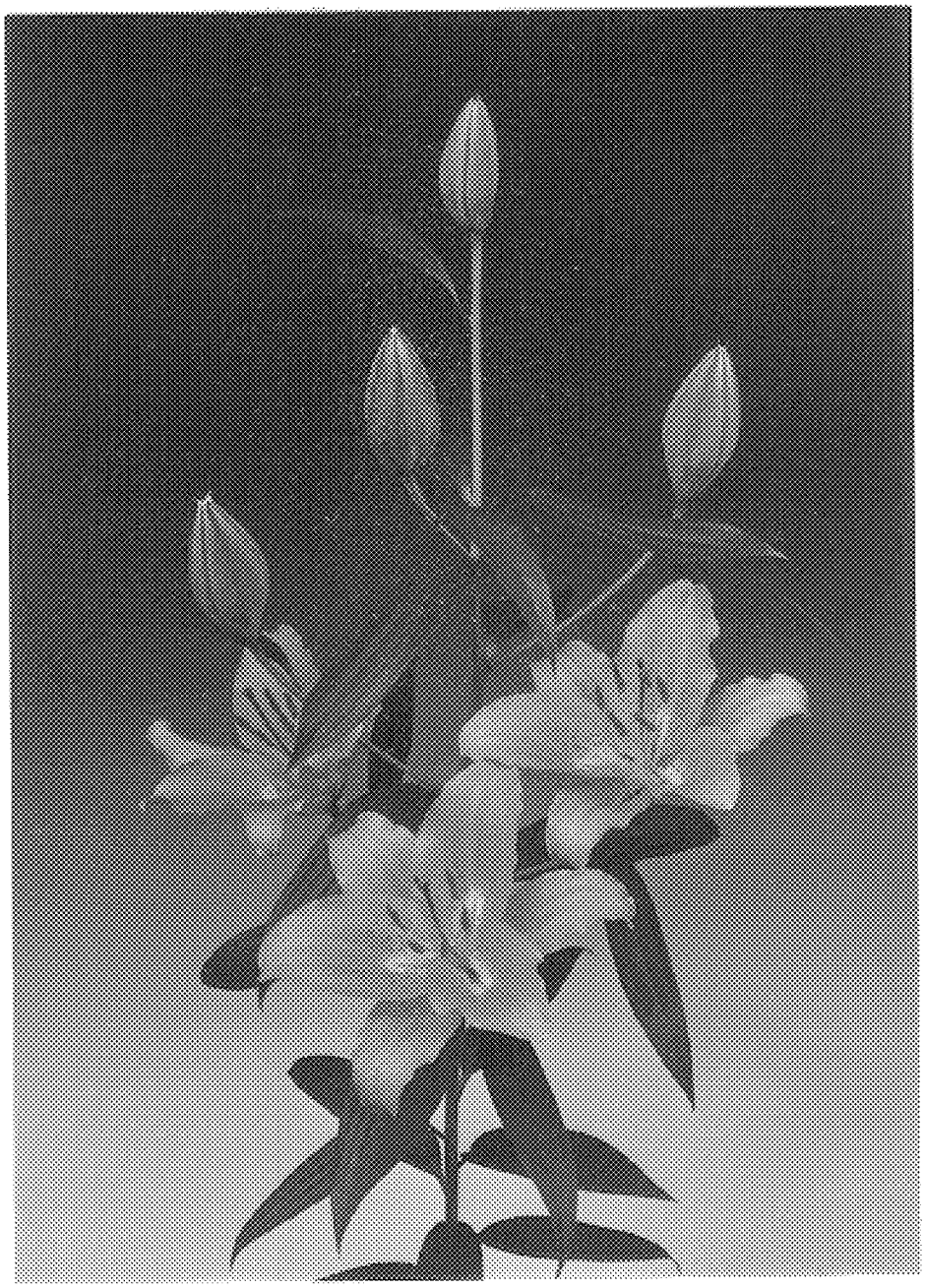

* * * * *